United States Patent
Kudielka et al.

(10) Patent No.: US 10,048,347 B2
(45) Date of Patent: Aug. 14, 2018

(54) POWER MEASUREMENT ON MAGNETIC RESONANCE IMAGING COIL AT DIFFERENT FREQUENCY THAN LARMOR FREQUENCY

(71) Applicant: GENERAL ELECTRIC COMPANY, Schenectady, NY (US)

(72) Inventors: Guido Peter Kudielka, Munich (DE); Pierre-Andre Vuissoz, Nancy (FR); Jacques Felblinger, Mereville (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 987 days.

(21) Appl. No.: 14/324,334

(22) Filed: Jul. 7, 2014

(65) Prior Publication Data

US 2016/0003927 A1   Jan. 7, 2016

(51) Int. Cl.
*G01V 3/00*      (2006.01)
*G01R 33/567*    (2006.01)
(Continued)

(52) U.S. Cl.
CPC .......... *G01R 33/5673* (2013.01); *A61B 5/055* (2013.01); *A61B 5/1126* (2013.01);
(Continued)

(58) Field of Classification Search
CPC ................................................. G01R 33/5673
(Continued)

(56) References Cited

U.S. PATENT DOCUMENTS 4,694,836 A   9/1987   Buikman et al.
4,712,560 A   12/1987  Schaefer et al.
(Continued)

FOREIGN PATENT DOCUMENTS

WO   2009098371 A2   8/2009
WO   2011030245 A1   3/2011

OTHER PUBLICATIONS

Guido P. Kudielka et al. "Usage of Birdcage Coil Harmonic Frequencies for Measurement of Respiration Induced Impedance Changes", References: [1] Buikman et.al., [1988], MRI 6(3):281-289. Abstract p. 1.

(Continued)

*Primary Examiner* — Louis Arana
(74) *Attorney, Agent, or Firm* — GE Global Patent Operation; Pabitra Chakrabarti (57) ABSTRACT

The system of the invention utilizes a magnetic resonance imaging (MRI) coil to measure power at a different frequency than the MRI frequency to produce MRI images. The different frequency such as harmonic frequency of the MR coil is applied to the coil and the reflected power is measured by the power sensor. Changes due to respiratory, cardiac, or overall motion are then analyzed, as desired. During imaging, the coil is connected to the MRI system and disconnected from the setup described, including the power sensor and its associated data processing, amplifier, signal generator, and directional coupler. Disconnect is provided in a one-step process by the switching circuit. Using the reflected power of a different frequency than the resonant frequencies of an MR coil improves signal information because it does not interfere with MR imaging process, is independent of patient and position, depicts the mechanical motion of the chest or organs near to the coil, and also measures irregular physiological activities with enough temporal resolution to describe these physiological changes.

22 Claims, 4 Drawing Sheets

(51) Int. Cl.
*A61B 5/00* (2006.01)
*A61B 5/055* (2006.01)
*A61B 5/11* (2006.01)
*G01R 33/36* (2006.01)
*G01R 33/34* (2006.01)
*G01R 33/565* (2006.01)

(52) U.S. Cl.
CPC ........ *A61B 5/7292* (2013.01); *G01R 33/3635* (2013.01); *G01R 33/3664* (2013.01); *G01R 33/34076* (2013.01); *G01R 33/56509* (2013.01)

(58) Field of Classification Search
USPC .................................................. 324/318, 322
See application file for complete search history.

(56) References Cited

U.S. PATENT DOCUMENTS

| | | | |
|---|---|---|---|
| 6,535,754 | B2 | 3/2003 | Fishbein et al. |
| 7,678,063 | B2 | 3/2010 | Felmlee et al. |
| 7,805,176 | B2 | 9/2010 | Ruppert et al. |
| 7,867,477 | B2 | 1/2011 | Driehuys et al. |
| 7,882,135 | B2 | 2/2011 | Brunner et al. |
| 8,285,359 | B2* | 10/2012 | Salla .................... A61B 5/7289 382/128 |
| 8,319,496 | B2 | 11/2012 | Eryaman et al. |
| 9,194,929 | B2* | 11/2015 | Siegert ............... G01R 33/5673 |
| 2010/0106008 | A1 | 4/2010 | Harvey |

OTHER PUBLICATIONS

Guido P. Kudielka et al. "Reflected Power as a Breathing Signal for Motion Correction in cMRI With GRICS", References: [1] Buikman et.al. [1988] MRI 6(3):281-289; [2] Odille et.al. [2007] IEEE Trans. Biomed. Eng. vol. 45:630-640; [3] Odille et al. [2008] MRM 60:146-157. Abstract p. 1.

O. Kosch et al. "Monitoring of Human Cardio-pulmonary Activity by Multi-Channel UWB-radar", 2011 IEEE, Abstract p. 1.

J. Vannesjo et al., "Correction of Breathing-induced Artefacts in High-Field Brain MRI Using Concurrent Field Monitoring", Proc. Intl. Soc. Magnetic Resonance Med., vol. 19, 2011, Abstract p. 1.

D. Buikman et al., "The RF Coil As a Sensitive Motion Detector for Magnetic Resonance Imaging", Magnetic Resonance Imaging, vol. 6, 1988, pp. 281-189.

I. Graesslin et al., "An Alternative Concept for Non-Sequence Interfering, Contact-free Respiration Monitoring", Proc. Intl. Soc. Magnetic Resonance Med., vol. 17, 2009, p. 753.

I. Graesslin et al., "Advancements in Contact-free Respiration Monitoring Using RF Pick-up Coils", Proc. Intl. Soc. Magnetic Resonance Med., vol. 18, 2010, p. 3045.

Graesslin et al., "An Alternative Concept of Selfnavigation for Patient Respiration Monitoring", Proceedings of the International Society for Magnetic Resonance in Medicine Scientific Meeting and Exhibition, vol. No. 15, pp. 867, 2007.

* cited by examiner

POWER MEASUREMENT ON MAGNETIC RESONANCE IMAGING COIL AT DIFFERENT FREQUENCY THAN LARMOR FREQUENCY

FIELD

The subject matter disclosed herein relates to magnetic resonance imaging (MRI), particularly as it relates to contactless techniques for acquiring respiration and cardiac gating waveforms for use in connection with MR imaging.

BACKGROUND

In the past, the MRI phenomenon has been utilized by structural chemists to study, in vitro, the molecular structure of organic molecules. Typically, MRI spectrometers utilized for this purpose were designed to accommodate relatively small samples of the substance to be studied. More recently, however, MRI has been developed into an imaging modality utilized to obtain images of anatomical features of live human subjects. Such images depicting parameters associated with nuclear spins (typically hydrogen protons associated with water in tissue) may be of medical diagnostic value in determining the state of health of tissue in the region examined. Thereby, energy is applied to the nuclear spins at a defined frequency, the Larmor frequency, and tissue related data is acquired at the same frequency by the dissipated energy as the nuclear spins regain their equilibrium. The use of MRI to produce images and spectroscopic studies of the human body has necessitated the use of specifically designed system components, such as the magnet, gradient and radio frequency (RF) coils.

In imaging techniques using the MRI phenomenon, the subject to be imaged remains motionless. Known imaging techniques, however, span time periods of typical heart and respiratory cycles, where movement of the subject is inevitable. A known method of avoiding distortion of an MR image from biological motion, such as heart and lung movement, is to gate acquisition of MRI signals to the cyclic movement of the heart or lungs. Unfortunately, in order to gate the acquisition of MRI signals to body movement such as heart or lung motion, probes have been placed on or in close proximity to the subject. This results in probes being placed inside the bore of the main magnet, an undesirable situation since the probes may often generate distortions in the uniform magnetic field $B_o$ and/or in the radio-frequency (RF) field, $B_1$, with a resulting reduction in image quality. Applying probes to the patient also reduces scanner throughput, thereby increasing the cost per scan.

Physiological signals are important parameters for MRI imaging, such as for gating and triggering sequences or retrospective image correction. Respiration information measured with a pneumatic belt is dependent on the belt position and belt sensitivity. Since breathing behavior varies between patients and can change on a patient during an MRI examination, a reliable measurement can be difficult. Further, in pediatric and neonatal imaging this technique can often not be used due to the lack of special pediatric equipment (e.g. smaller belts) or the physiological differences of a newborn.

In cardiac magnetic resonance imaging (e.g. cardiac MRI), the measurement of physiological parameters is used to trigger the imaging sequence, to monitor the patient, or to collect the data for post-processing purposes. Current techniques use pneumatic belt systems to acquire respiratory motion and utilize other sensors to acquire the electrocardiogram (ECG) for measurement of the cardiac activity as to heart movement. The reliability of the ECG, however, often suffers from electromagnetic fields applied during the imaging sequence or by the electromagnetic effects on the blood. Furthermore, ECG represents the electrical activity of the heart rather than the mechanical contraction.

One contactless method utilizes a respiratory belt with wireless data transfer. Another contactless method uses the impedance change of the transmission coil caused by chest movement. This causes a shift of the resonance frequency which leads to alteration of the reflected power on the excitation frequency. This method solves the position dependence of the pneumatic belt, but is limited, however, in sampling rate and data volume, as caused by its strong dependence on the repetition time of the sequence and the number of excitation pulses. Another contactless method uses nuclear magnetic resonance (NMR) pick-up coils (PUC) to measure the impedance change independently from the imaging coil. Another contactless method is described, where a second coil inside the MRI imaging coil is used for the impedance change measurements. Thereby the second coil has a much higher frequency than the MRI imaging coil. Another contactless method is described by the usage of ultra-wideband radar (UWB), where frequencies in the GHz range are utilized.

Aside from physiological signals, bulk motion further degrades the image quality. It will therefore be useful for a system to provide overall measurement of motion that can be applied to prospective motion correction or scan interruption. The system will address improvement of signal information, including sensitivity and reliability of physiological data. As follows, the invention addresses the needs thus described.

SUMMARY

The above and other drawbacks or deficiencies may be overcome or alleviated by development of a system as described as follows. In embodiments of the following, power is measured on the coil at a different frequency than the magnetic resonance frequency for acquisition of physiological signals.

Embodiments of the invention include a method of acquiring data related to motion of a subject with a coil of a magnetic resonance imaging (MRI) system for use in the acquisition of MR data for imaging a region of the subject, said method comprising the steps of: providing an MRI system having a first signal generator, the coil arranged with radio-frequency components; assembling a setup to include a second signal generator, an amplifier, a directional coupler, a power sensor, a data processing system, and a logic circuit in combination with a switching circuit, wherein the MRI system is interconnected with the setup by way of the switching circuit; applying at least a first resonance frequency to the coil from the first signal generator of the MRI system, wherein the first resonance frequency is an imaging frequency; tuning at least a second resonance frequency to the coil, wherein the second resonance frequency is a predetermined frequency generated from the second signal generator external to the MRI system, the predetermined frequency at a mode applied for measurement of a physiological attribute associated with the subject, wherein the predetermined frequency is a different frequency than the imaging frequency; directing the signal through the amplifier and adjusting signal gain by the amplifier; routing the signal through the directional coupler; measuring reflected power from the coil by way of the power sensor; decoupling from the coil during MRI radio-frequency (RF) excitation and measurement; and processing data by way of the data processing system for visualization and storage; wherein the imaging frequency is used to generate imaging data and wherein the predetermined frequency is used to measure impedance directly on the coil.

In one embodiment, the method further comprises a step of analyzing the MRI RF excitation and measurement through the logic circuit and communicating results to the switching circuit. In another embodiment, the method acquires data related to motion of a subject with a coil, such as a birdcage coil, of an MRI system for use in the acquisition of MR data for imaging a region of the subject. In one aspect, the step of processing data includes filtering and normalizing data by way of the data processing system for visualization, storage, and use in the reconstruction of MRI images or to trigger the MRI system. In one aspect, the method includes analyzing MRI radio-frequency excitation and measurement by the logic circuit. In another aspect, the method includes routing the signal through a switching circuit. In another aspect, the method comprises disconnecting the source signal from the coil, typically in a one-step process. In one embodiment, any RF coil is used in the system, including a birdcage coil. For exemplary purposes, and not limitation, in a multi-transmit system, the coil is not formed by a single birdcage coil, but by several elements acting as independent coils. For exemplary purposes, and not limitation, in an independent transmit received system, the RF coils of the receiving system can be used as probing coil.

In one embodiment, a motion detection system is disclosed for monitoring a range of physiological motion of a subject, the system comprising: a signal generator that produces a signal of a predetermined frequency at a mode applied for measurement of a physiological attribute associated with the subject, wherein the predetermined frequency is a harmonic frequency applied to the coil, or any frequency of a particular coil in a multi-transmit system that is different than the resonant frequency used for MRI; an amplifier that adjusts signal gain as the signal passes therethrough; a directional coupler through which the signal is routed; a coil connected to radio-frequency components of an MRI system; a power sensor that measures reflected power from the birdcage coil; a data processing system to filter and store data and send it to an appropriate device such as the MRI system, to account for overall motion of the subject; and a logic circuit that analyzes excitation states during imaging; wherein the signal generator, the amplifier, the directional coupler, the power sensor, the data processing system, and the logic circuit form a setup to account for overall motion of the subject, the setup operating in combination with a switching circuit such that MRI imaging data is acquired at a designated region of the subject when the coil, or birdcage coil, is connected to the MRI system and disconnected from the setup; and wherein the different frequency is a non-Larmor frequency.

In one aspect, the physiological attribute is motion of regular (e.g. cardiac or respiratory motion) and irregular physiological activities (e.g. swallowing, eyeblinking, etc). In another aspect, the states of excitation are provided by the MRI system and analyzed by the logic circuit.

Embodiments of the invention provide a Larmor imaging frequency and a predetermined frequency (non-Larmor) different from the imaging frequency. In one aspect, the predetermined frequency is produced by the signal generator external to the MRI system's signal generator. In another aspect, the signal generator of the MRI system can be modified to provide both a Larmor imaging frequency and a predetermined non Larmor frequency that originates within the MRI system. As such, this type of latter option could be implemented in current MRI systems. The separate second signal generator external to the system also allows generation of imaging data by the imaging frequency and measurement of impedance directly on the coil, as can be implemented with MRI designs. As such, in one aspect, the method includes the step of generating a signal while utilizing a second signal generator external to the MRI system and interconnected with the setup to produce the second resonance frequency.

DETAILED DESCRIPTION

Various embodiments will be described more fully hereinafter with reference to the accompanying drawings. Such embodiments should not be construed as limiting. For example, one or more aspects can be utilized in other embodiments and even other types of devices. Referring to the drawings in general, it will be understood that the illustrations are for the purpose of describing particular embodiments and are not intended to be limiting.

In an embodiment of the invention, a birdcage coil having multiple resonant frequencies, also known as harmonic frequencies or modes, or non-Larmor frequencies, is utilized to measure respiratory induced impedance changes. In one aspect, the harmonic frequency refers to the frequency as utilized with the birdcage coil. In another aspect, when utilizing any coil, a resonance frequency different from the Larmor imaging frequency is referenced, such as when the coil is actively detuned. Further, other coils that provide more resonant frequencies besides the Larmor frequency, for instance, by detuning circuits can be utilized. More broadly, any frequency of a particular coil in a multi-transmit system may be used that is different than the resonant frequency used for the MRI imaging. The technique provides a contactless respiration and cardiac acquisition as well as global motion detection with high sampling rate during MRI imaging. Since the contactless measurement of the physiological data is performed on the same coil used for the imaging process (excitation of the nuclear spins and/or acquisition of the signal from the nuclear spins), there is no need for additional coils or RF probes on or around the subject. Although this embodiment shows the usage of a birdcage coil, other coils that provide more resonant frequencies besides the Larmor frequency (e.g. by detuning circuits) can be used.

For MRI imaging, resonant coils are used to excite the hydrogen protons and to acquire the signal from the human body. The capacitance and inductance of the coils are chosen such that the coil impedance is tuned for a specific frequency, specifically, the Lamor frequency of hydrogen, or 1H-frequency. In resonance, the coil impedance is equal to the resistance since the capacitive and inductive reactance cancel out. When a human is placed near to the coil, the human body acts as an RLC circuit (as defined by a circuit comprising a resistor, an inductor, and a capacitor, connected in series or in parallel) which changes the total impedance and the resonant frequency of the coil. In one aspect, the circuit forms a harmonic oscillator.

Here, for exemplary purposes and not limitation, the placement of a human near the coil changes the load of the harmonic oscillator formed by the birdcage coil, mostly by capacitive coupling. The applied power on the original frequency then is no longer fully transmitted by the coil and partially reflects back to the source. The impedance change is distance dependent; in other words, the chest motion caused by respiration or cardiac movement leads to impedance changes and different reflected power levels. Using the excitation RF pulse of an MRI sequence for impedance change measurement, the sampling and data rate depends on the repetition time (TR) and the number of excitation pulses such that the typical sampling rate ranges between 2 and 0.5 samples per second.

Figure 2:
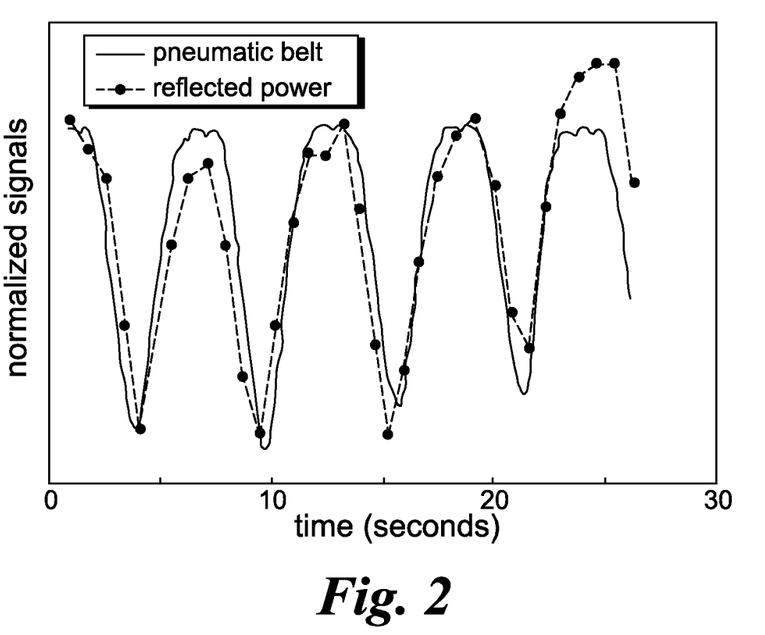
FIG. 2 depicts the reflected power caused by impedance changes during RF transmission inside a birdcage coil as considered as an input breathing signal for retrospective motion correction, such as GRICS reconstruction.

FIG. 2 shows a comparison of the reflected power of a birdcage coil with the breathing state information from a pneumatic belt. While comparing the reflected power of a birdcage coil with the breathing state information from a pneumatic belt, the embodiment suffices for respiratory detection; the embodiment, however, does not allow for cardiac motion detection. This is resolved by sampling continuously or partial continuously on a resonance [harmonic] frequency of the MRI coil which is different from the 1H-frequency.

Figure 1:
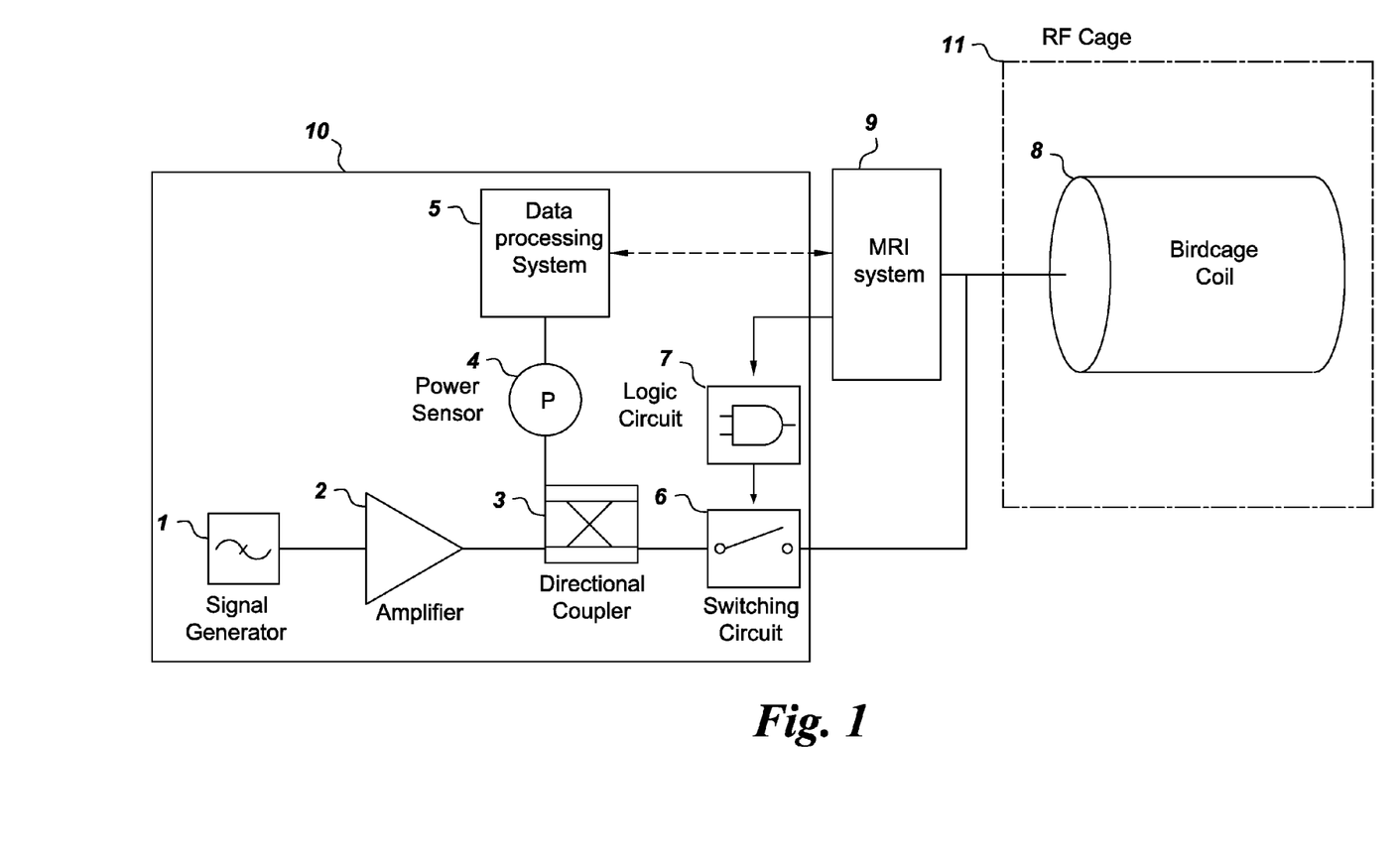
FIG. 1 depicts a schematic of an embodiment of the present invention.

In one embodiment of the invention, as shown in FIG. 1, a magnetic resonance imaging (MRI) system 10 is utilized to measure different frequencies such as the 1H-frequency on an MRI coil 8. As illustrated, the system includes a signal generator 1, or high-frequency source 1, that generates a signal at the mode which is applied for respiration measurement. In one embodiment, to measure on an MRI birdcage coil 8, different frequencies from the 1H-frequency are utilized. The signal gain is adjusted by an amplifier 2 and routed through a directional coupler 3. A power sensor 4 on the reflected path measures and digitizes the reflected power of the coil 8. The data is filtered and processed by a data processing system 5 for visualization and/or storage afterwards or the data can be directed to the MRI scanner/system 9 for triggering or gating purposes (designated by ← -- -- -- →). The measurement setup 1-7 is connected to the MRI coil 8 by a switching circuit 6. The switching circuit disconnects the setup 1-7, including the signal generator, amplifier, and directional coupler, from the coil during excitation and sampling of data at the 1H-frequency. The definitions of the states of excitation are provided by the MRI system and analyzed by the logic circuit 7 to control the opening of the switch 6, and optionally, switch off the amplifier 2. In other words, the MRI system informs the setup on the timing of when the measurement can be performed. In practicality, a transistor-transistor logic (TTL) impulse is sent to blank the measurement when the RF power is transmitted to the birdcage coil 8 from the MR system 9. In one aspect, the coil 8 is placed in an RF cage, or Faraday cage 11, to further suppress RF signals from the environment.

In one embodiment, the circuit is implemented as a switch. In another embodiment, the circuit is modified as a passive narrow band splitter that directs various frequencies which can be designed in accordance with the objectives of the invention.

In process, the non-Larmor frequency, also referred to as harmonic frequency, is applied to the coil 8 and the reflected power is measured by the power sensor 4. As described in embodiments of the invention, amplifier 2 gains the power of the signal of signal generator 1. This amplified signal runs to coil 8 via directional coupler 3 and/or switching circuit 6. Power sensor 4 measures the reflected part of this power from coil 8 via switching circuit 6 and directional coupler 3.

In one aspect, the power is reflected back at an entry port of coil 8 through switching circuit 6 and directional coupler 3, and diverted to power sensor 4 where the measurement occurs. The link between data processing system 5 and MR system 9 is an information transfer link, not a physical measurement connection. Changes due to respiratory, cardiac, or global overall motion are then analyzed, as desired. During imaging, as defined as the "states of excitation", the birdcage coil is connected to the MRI system and disconnected from the setup described, including disconnect from the power sensor and its associated data processing, amplifier, signal generator, and directional coupler. In one embodiment, disconnect is provided in a one-step process by the switching circuit 6. In one aspect, the signal generator 1 is driven in continuous mode; in another aspect, the signal generator is operated in pulsed mode. In another aspect, other sources of information coming from different physiological sensors, such as from ECG or respiratory belt mentioned above, are also collected in the data processing unit and combined with the reflecting power physiological signal. With this method, an overall measurement of motion inside the coil is possible, which is applied to corrective actions such as prospective motion correction or scan interruption.

Using the reflected power of resonant frequencies of a coil improves signal information because it is independent of position, depicts the mechanical motion of the chest or organs near to the coil, and also measures irregular physiological activities such as swallowing, bulk head or body motion. The additional benefits of the system allow the reflected power data to be used in addition to existing methods to improve sensitivity and reliability of physiological data.

In another aspect, reflected power measurement replaces existing methods by reducing the patient preparation time and patient comfort. Further, embodiments of the invention are implemented with neonatal MRI systems to improve measurement of respiration in a neonate or child. Furthermore, enhanced techniques implement the motion correction system for cardiac MRI. The systems provide benefits as to precise physiological data with increased accuracy of the corrected image data, including without limitation, post-processing techniques. In one aspect, the invention is used as an acquisition system for external physical measurements.

In one aspect, the MRI coil may be defined as a transmit unit that is a surface coil or part of a surface coil. For exemplary purposes, and not limitation, the transmit unit may be a birdcage coil or loop of a multi-element coil. The transmit coil may also include a multi-element transmit coil and one or several elements may be used in transmission of harmonics or in reception of the transmitted power.

In another aspect, the sensor unit does not measure RF power, but instead measures other characteristics of the reflected signal such as phase, amplitude, or envelope shape, alone or in combination. Further, the phase, amplitude, or envelope shape may be measured along with RF power.

In one aspect, the switching circuit may be replaced to protect the non-Larmor frequency setup from the MRI system. For example, instead of detuning, the coil may be actively tuned to the specific harmonic frequency when not in charge of excitation. Further, embodiments of the invention may be incorporated into the MRI system such that existing MRI components are configured to function with the harmonic frequency setup. For example, an additional exciter as used for the multi-nuclear spectroscopy (MNS) option may deliver the frequency and power for the non-Larmor frequency; other parts of this subsystem as well may be used for the measurement assembly. In yet another aspect, non-harmonic frequencies may be applied in the GHz range, where motion is recognized. The system, as designed by the current implementation of the setup, however, is not restrained to use of low band radio-frequency. In one embodiment, the measurement can be implemented at any frequency, such as when using the MR system coil as an element of a scanner in the GHz range (e.g. as one commonly used in an airport for surface body investigation).

Furthermore, the pathway may be modified. In one embodiment, the pathway progresses from the amplifier 2→directional coupler 3→switching circuit 6→MRI coil 8 and reflects as MRI coil 8→switching circuit 6→directional coupler 3→power sensor 4. This pathway may be entirely separated with independent transmit and acquisition channels. In addition, the sensor 4 may be placed directly on the coils or voltmeter that measures the tension in the capacitor.

Further, in embodiments of the invention, impedance changes caused by respiration are measured by the reflection of the transmitted power. In one aspect, the reflected power of the RF transition at resonance frequency of a proton is used along with the post-processing system. The present invention incorporates use of another frequency, different from the one used for MRI. Since the sampling rate depends on RF excitation, sequences with multiple RF pulses (e.g. SSFP) or short TR could improve the sampling accuracy.

Usage of Birdcage Coil Harmonic Frequencies: Measurement of Respiration Induced Impedance Changes Respiration induced impedance changes (RIIC) in a birdcage coil can be acquired by reflected power measurements during RF transmission. The dependence on the excitation pulse, however, limits the sampling and data rate. As described in another embodiment of the invention, continuous measurement of the Respiration Induced Impedance Changes (RIIC) were performed with the usage of a harmonic frequency of the birdcage coil.

Method:

The resonant spectrum of a 3T MRI birdcage body coil was measured with a network analyzer. The S11-characteristic and Q-values of the harmonic modes were analyzed. In one embodiment, the S11-characteristics of a coil, indicating the tuning of the coil to a certain frequency, provide the harmonic frequencies. In a linear two port network, incident power and reflected power are linked by the S-parameter matrix. Therefore, the S11-characteristic is the coefficient that links the incident power at a first port to the reflected power at the same port. The quality factor, or Q-value, shows the bandwidth of the resonance frequency, whereas the bandwidth is reciprocal to this value. If the bandwidth is small, the Q-value is high; therefore the sensitivity to the impedance change is high (and vice versa). An external RF source was connected to the I-port of the body coil, while the Q-port was terminated. A frequency multiplier and amplifier were used to generate the different frequencies with a constant power at the coil of $P_{FWD}=10$ mW (where $P_{FWD}$ is the forward power). The reflected power was measured with a power sensor via a directional coupler.

Figure 3:
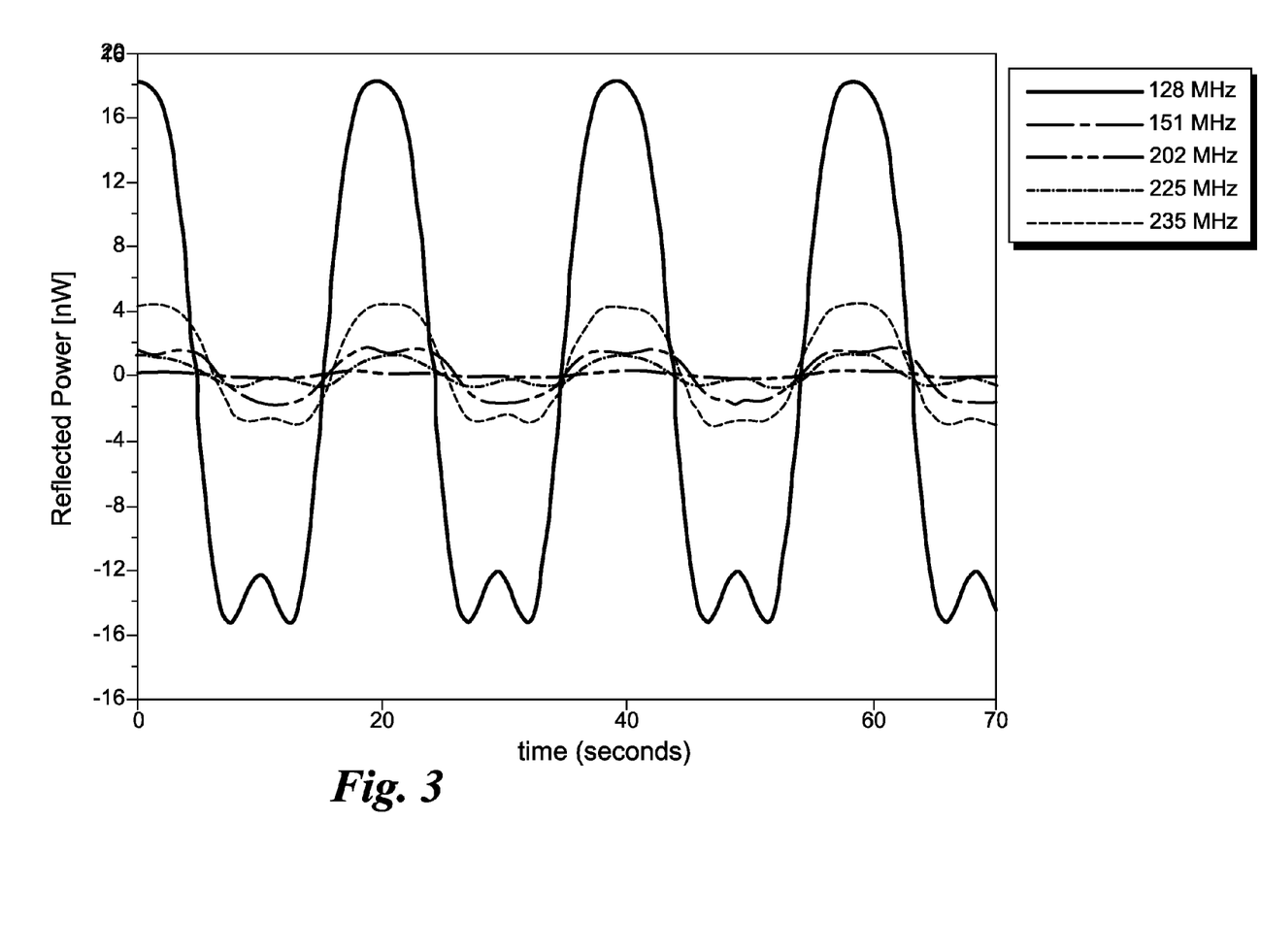
FIG. 3 demonstrates the reflected power measured with a power sensor via a directional coupler, the reflected power of harmonic frequencies of a birdcage coil during phantom movement.

The effect of the impedance change caused by a moving $CuSO_4$-phantom was evaluated for the harmonic frequencies as designated in FIG. 3, as depicted, reflected power of harmonic frequencies during phantom movement. The best correlation (higher Q-value) between impedance change and reflected power was measured at a frequency of 235 MHz besides the 1H-frequency for this specific coil. This frequency was used to measure RIIC on a healthy subject in the birdcage coil. For comparison, the information of the pneumatic belt was also saved. The data were filtered and processed using analytical software. In one aspect, the measured power data was normalized and filtered by a windowed, linear-phase finite impulse response (FIR) filter. The filter band was set for a center frequency of 0.125 Hz with a bandwidth of +/−0.025 Hz in a Hamming-window design and a filter order of 199. Since the reference data from the pneumatic belt was pre-processed by the MRI system, no further data processing besides normalization for regression analysis was applied. Note that in comparison of the harmonic frequencies, the one with the highest Q-value was chosen for the measurement because this frequency reacts most on impedance changes. Technically, any harmonic frequency may be utilized and encompassed in the method and system of the invention.

Figure 4:
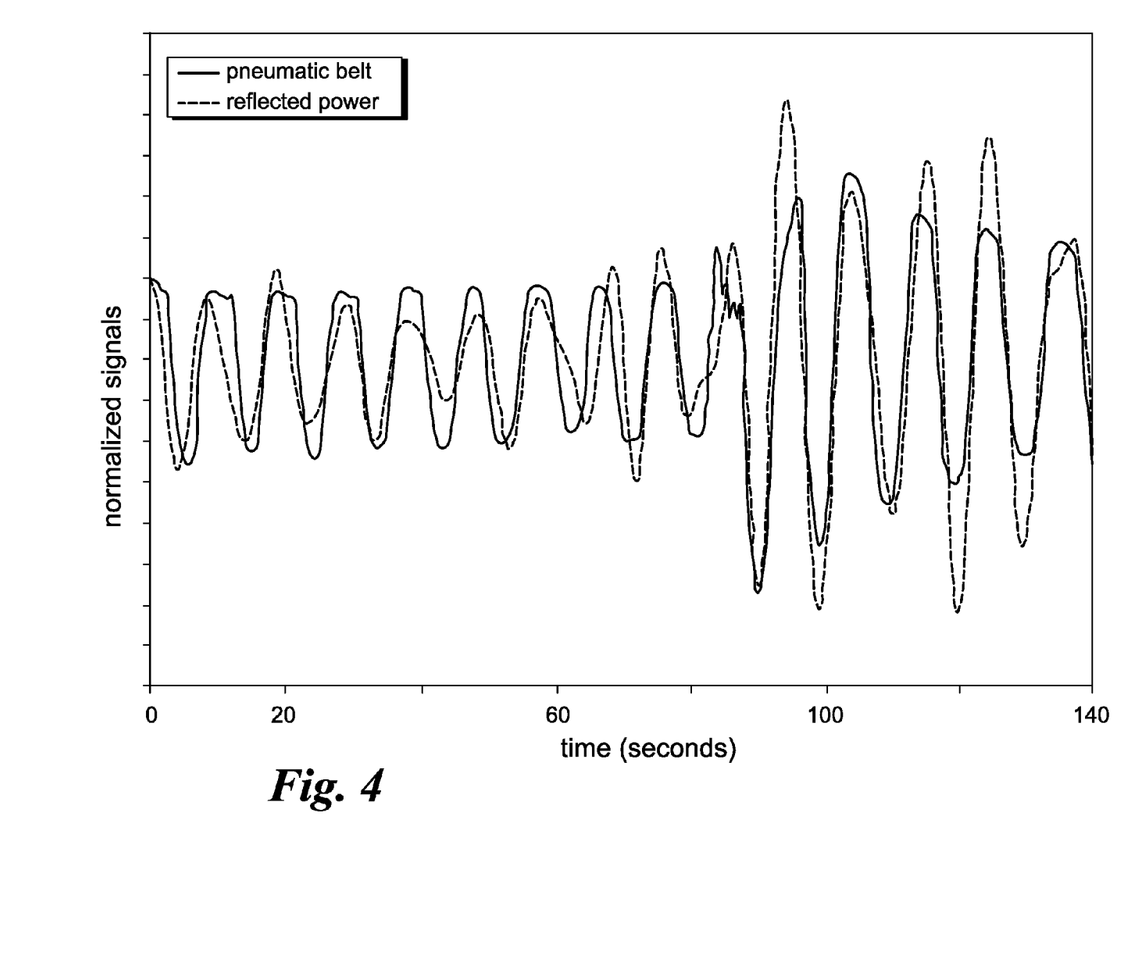
FIG. 4 demonstrates an embodiment of the invention in reference to Respiration Induced Impedance Changes (RIIC) measured at 235 MHz and correlated ($R^2$=0.73) to the respiratory belt data.

Results:

The RIIC measured at 235 MHz shows good correlation ($R^2=0.73$) to the respiratory belt data, as shown in FIG. 4. As illustrated, normalized pneumatic belt data and reflected power at f=235 MHz during normal breathing (0-90 sec) and deep breathing (90-140 sec) are compared.

Due to a lower Q-value of the harmonic frequencies, the reflected power changes are not as dominant as on the tuned 1H-frequency. After filtering on the respiration frequency of 0.1 Hz and normalization of the data, however, the RIIC was detected reliably and magnitude differences between normal and deep breathing were distinguished.

As demonstrated in the usage of birdcage coil harmonics, no additional sensors inside the magnet room or on the patient itself are needed to detect respiratory movement. In addition, the continuous acquisition of the reflection changes on a harmonic frequency allows a high resolution sampling of the RIIC, which can be used for motion correction. For synchronous imaging and RIIC measurement, a fast switching unit (e.g. pin-diode circuit) may be used to prevent the measurement setup from the high power of the 1H-excitation pulse.

Various embodiments of the invention designate novelty in the usage of birdcage coil harmonics for RIIC measurement, as shown. Furthermore, embodiments of the invention may also provide for imaging during the measurement, as well as to acquire and analyze cardiac induced impedance changes for motion correction or triggering. Furthermore, embodiments of the invention may use the respiratory signal for gating MRI sequences, whereas the RF excitation and image acquisition is performed during a specific respiratory phase. The phase is defined by user-selected thresholds.

While the invention has been described in considerable detail with reference to a few exemplary embodiments only, it will be appreciated that it is not intended to limit the invention to these embodiments only, since various modifications, omissions, additions and substitutions may be made to the disclosed embodiments without materially departing from the scope of the invention. In addition, many modifications may be made to adapt to a particular situation or an installation, without departing from the essential scope of the invention. Thus, it must be understood that the above invention has been described by way of illustration and not limitation. Accordingly, it is intended to cover all modifications, omissions, additions, substitutions or the like, which may be comprised within the scope and the spirit of the invention as defined by the claims.

The invention claimed is:

1. A method of acquiring data related to motion of a subject with a coil of a magnetic resonance imaging (MRI) system for use in the acquisition of MR data for imaging a region of the subject, said method comprising the steps of:
providing an MRI system having a first signal generator, the coil arranged with radio-frequency components;
assembling a setup to include a second signal generator, an amplifier, a directional coupler, a power sensor, a data processing system, and a logic circuit in combination with a switching circuit, wherein the MRI system is interconnected with the setup by way of the switching circuit; applying at least a first resonance frequency to the coil from the first signal generator of the MRI system, wherein the first resonance frequency is an imaging frequency;
tuning at least a second resonance frequency to the coil, wherein the second resonance frequency is a predetermined frequency generated from the second signal generator external to the MRI system, the predetermined frequency at a mode applied for measurement of a physiological attribute associated with the subject, wherein the predetermined frequency is a different frequency than the imaging frequency;
directing the signal through the amplifier and adjusting signal gain by the amplifier;
routing the signal through the directional coupler;
measuring reflected power from the coil by way of the power sensor;
decoupling from the coil during MRI radio-frequency (RF) excitation and measurement; and
processing data by way of the data processing system for visualization and storage;
wherein the imaging frequency is used to generate imaging data and wherein the predetermined frequency is used to measure impedance directly on the coil.

2. The method of claim 1, further comprising a step of analyzing the MRI RF excitation and measurement through the logic circuit and communicating results to the switching circuit.

3. The method of claim 2, further comprising a step of directing the data to the MRI system for gating purposes.

4. The method of claim 3, wherein the step of measuring includes digitizing the reflected power of the coil.

5. The method of claim 4, wherein said step of routing further comprises routing the signal of predetermined frequency through a switching circuit.

6. The method of claim 5, further comprising disconnecting the source of the signal from the coil.

7. The method of claim 6, wherein the step of disconnecting occurs during excitation and sampling of imaging data.

8. The method of claim 6, wherein the step of disconnecting occurs during excitation and sampling of imaging data at the 1H-frequency.

9. The method of claim 8, wherein said step of analyzing, changes due to respiratory, cardiac, and overall motion are analyzed, alone or in combination.

10. The method of claim 1, wherein the coil is connected to the MRI system when not imaging and disconnected from the setup during said step of providing an imaging frequency from the MRI system to the coil.

11. The method of claim 1, wherein the coil is a birdcage resonator.

12. The method of claim 1, wherein the signal generator operates in continuous or pulsed modes.

13. The method of claim 1, wherein said step of processing data includes overall measurement of motion inside the coil.

14. The method of claim 13, wherein the step of processing data includes normalizing and filtering data as applied to corrective actions such as prospective motion correction or scan interruption, alone or in combination.

15. A motion detection system for monitoring a range of physiological motion of a subject comprising:
a magnetic resonance imaging (MRI) system that produces an imaging frequency to a coil, wherein the coil is internal to the MRI system;
a signal generator that produces a signal of a predetermined frequency at a mode applied for measurement of a physiological attribute associated with the subject, wherein the predetermined frequency is a different frequency than the imaging frequency applied to the coil;
an amplifier that adjusts signal gain as the signal passes therethrough;
a directional coupler through which the signal is routed;
a plurality of radio-frequency (RF) components surrounding the subject in the MRI system;
a power sensor that measures reflected power from the coil;
a data processing system to filter and store data; and
a logic circuit that analyzes excitation states during imaging, the excitation states provided by the MR system;
wherein the signal generator, the amplifier, the directional coupler, the power sensor, the data processing system, and the logic circuit form a setup to account for overall motion of the subject that operates in combination with a switching circuit such that imaging data is acquired at a designated region of the subject when the coil is connected to the MRI system and disconnected from the setup; and wherein the different frequency is a non-Larmor frequency.

16. The system of claim 15, wherein the power sensor on the reflected path measures and digitizes the reflected power of the coil.

17. The system of claim 16, wherein the signal generator generates a signal at a mode as applied to a designated physiological attribute.

18. The system of claim 17, wherein the physiological attribute includes regular and irregular physiological activities.

19. The system of claim 18, wherein the physiological attribute includes one or more of bulk motion, respiratory motion or cardiac motion, alone or in combination.

20. The system of claim 15, wherein the imaging frequency and the different frequency produced by the signal generator originate within the MRI system.

21. A method of acquiring data related to motion of a subject with a coil of a magnetic resonance imaging (MRI) system for use in the acquisition of MR data for imaging a region of the subject, said method comprising the steps of:
providing an MRI system to include a signal generator and arranging the coil with radio-frequency components, wherein the MRI system is interconnected with the setup by way of a switching circuit;

assembling a setup to include the signal generator, an amplifier, a directional coupler, a power sensor, a data processing system, and a logic circuit in combination with the switching circuit;

applying at least a first resonance frequency to the coil, wherein the first resonance frequency is an imaging frequency generated from the signal generator;

generating a signal from the signal generator to produce at least a second resonance frequency, wherein the second resonance frequency is a predetermined frequency generated from the signal generator, the predetermined frequency at a mode applied for measurement of a physiological attribute associated with the subject, wherein the predetermined frequency is a different frequency than the imaging frequency;

applying the predetermined frequency to the coil, directing the signal through the amplifier and adjusting signal gain by the amplifier;

routing the signal through the directional coupler;

measuring reflected power from the coil by way of the power sensor;

decoupling from the coil during MRI radio-frequency (RF) excitation and measurement; and processing data by way of the data processing system for visualization and storage;

wherein the imaging frequency generates imaging data and wherein the predetermined frequency is used to measure impedance directly on the coil.

22. The system of claim 21, wherein the step of generating a signal utilizes a second signal generator external to the MRI system and interconnected with the setup to produce the second resonance frequency.

* * * * *